US011213421B1

(12) United States Patent
Fuisz et al.

(10) Patent No.: US 11,213,421 B1
(45) Date of Patent: Jan. 4, 2022

(54) DEVICE AND METHOD FOR REDUCING URINARY RETENTION

(71) Applicants: Joseph M. Fuisz, Nashville, TN (US); Richard C. Fuisz, Franklin, TN (US)

(72) Inventors: Joseph M. Fuisz, Nashville, TN (US); Richard C. Fuisz, Franklin, TN (US)

( * ) Notice: Subject to any disclaimer, the term of this patent is extended or adjusted under 35 U.S.C. 154(b) by 0 days.

(21) Appl. No.: 17/342,272

(22) Filed: Jun. 8, 2021

(51) Int. Cl.
*A61F 5/453* (2006.01)
*A61F 5/44* (2006.01)

(52) U.S. Cl.
CPC ........... *A61F 5/453* (2013.01); *A61F 5/4404* (2013.01)

(58) Field of Classification Search
CPC ........ A61F 5/451; A61F 5/4404; A61F 5/453; A61B 10/007; A61G 9/00; A61G 9/003; A61G 9/006
See application file for complete search history.

(56) References Cited

U.S. PATENT DOCUMENTS

| | | | | |
|---|---|---|---|---|
| 651,310 | A * | 6/1900 | Hogan | A61G 9/003 4/450 |
| 920,463 | A * | 5/1909 | Hogan | A61G 9/003 4/450 |
| 1,237,483 | A * | 8/1917 | Darnall | A47K 11/04 4/483 |
| 1,801,030 | A * | 4/1931 | Vasse | A61G 9/006 4/455 |
| 2,594,339 | A * | 4/1952 | Nugent | A61G 9/006 4/144.1 |
| 3,479,671 | A * | 11/1969 | Beich | A61G 9/006 4/144.1 |
| 4,665,571 | A * | 5/1987 | Muccione | A61G 9/006 4/114.1 |
| 5,926,858 | A * | 7/1999 | Heller | A47K 11/12 4/144.1 |
| 11,045,296 | B1 * | 6/2021 | Mohamed | A61F 2/004 |
| 2005/0066432 | A1 * | 3/2005 | Gouldsworthy | G01F 19/00 4/450 |

(Continued)

OTHER PUBLICATIONS

List of thermal conductivities. https://www.chemeurope.com/en/encyclopedia/List_of_thermal_conductivities.html. Accessed Jul. 21, 2021.*

(Continued)

*Primary Examiner* — Adam Marcetich
(74) *Attorney, Agent, or Firm* — Fitch, Even, Tabin & Flannery, LLP

(57) ABSTRACT

A device to facilitate urination by a male includes a vessel having a contact surface area at and adjacent a top edge of the vessel configured to be placed in contact with the penis. The contact surface area includes a thermally conductive material and has a shape configured to reduce hydrostatic pressure requirements for urination from a standing position as compared with urinating into a toilet from a standing position. A method of reducing urinary retention in a male includes contacting the penis of the male with a contact surface area of a device, which may be as described above, and urinating while the male is in a standing position with the penis in contact with the contact surface area, wherein the contact surface area comprises a thermally conductive material and is at an initial temperature at least 14° F. lower than a temperature of the penis.

24 Claims, 5 Drawing Sheets

(56) References Cited

U.S. PATENT DOCUMENTS

| | | | | |
|---|---|---|---|---|
| 2009/0105793 A1* | 4/2009 | Brown | ............... | A61F 7/02 |
| | | | | 607/108 |
| 2013/0261419 A1* | 10/2013 | Davidson | ........... | A61B 5/14532 |
| | | | | 600/365 |
| 2014/0303584 A1* | 10/2014 | Keating | ................ | A61G 9/006 |
| | | | | 604/378 |
| 2016/0095479 A1* | 4/2016 | Jenkin | ................ | A61F 5/453 |
| | | | | 4/144.1 |

OTHER PUBLICATIONS

Fowler, Clare J., Derek Griffiths, and William C. De Groat. "The neural control of micturition." Nature Reviews Neuroscience 9.6 (2008): 453-466. (Year: 2008).*

Geirsson, Gudmundur, Sivert Lindström, and Magnus Fall. "The bladder cooling reflex and the use of cooling as stimulus to the lower urinary tract." The Journal of urology 162.6 (1999): 1890-1896. (Year: 1999).*

Al-Hayek, Samih, and Paul Abrams. "The 50-year history of the ice water test in urology." The Journal of urology 183.5 (2010): 1686-1692. (Year: 2010).*

* cited by examiner

DEVICE AND METHOD FOR REDUCING URINARY RETENTION

BACKGROUND OF THE INVENTION

Benign prostatic hyperplasia (BPH) typically begins after the age of forty, and half of males fifty and over are affected. By the age of eighty, 90% of males are affected.

Various pharmacological treatments exist, including, inter alia, alpha blockers such as tamsulosin, 5α-reductase inhibitors such as finasteride, and phosphodiesterase type 5 inhibitors, such as tadalafil. Unfortunately, pharmacological treatments are not always completely sufficient to the task.

Various surgical and non-surgical interventions are also employed, such as prostate surgery, including inter alia the use of devices like Urolift®. Urolift® is an FDA-approved implanted device placed through the obstructed urethra, and placed permanently to hold the enlarged prostate tissue out of the way and increase the opening of the urethra.

Other interventional procedures include transurethral microwave therapy (TUMT). TUMT employs a microwave antenna attached to a flexible tube that is inserted into the bladder, and microwave heat is used to kill off excess prostate tissue.

Laser surgery is also used to destroy prostate tissue and shrink the gland.

Transurethral incision of the prostate (TUIP) is another surgical solution. It involves cuts being made in the prostate to reduce the prostate's pressure on the urethra, and may be recommended for smaller prostates. One downside is the frequent need to repeat the procedure.

The most common surgery for BPH is transurethral resection of the prostate (TURP). In TURP, the physician removes portions of the prostate using a scope inserted through the urethra.

These various surgical interventions involve known side effects, some of which are serious and have adverse quality of life implications.

BPH is characterized by a spectrum of obstructive and irritative symptoms, known collectively as LUIS (lower urinary tract symptoms). Poor urinary flow and the sensation of incomplete bladder emptying are the two symptoms that correlate most closely with the eventual need for prostate surgery. Untreated, a significant number of men with BPH will eventually develop acute urinary retention.

Urinary catheters are frequently used to empty the bladder where the bladder is not voided adequately by the patient, and in some cases patients will be asked to self-administer catheters. This is obviously painful, uncomfortable, inconvenient, and demoralizing.

The demoralizing aspects of poor urine streams and sleep interruption should not be discounted as a critical quality of life issue for afflicted men.

It is noted that BPH is not the sole cause of urinary retention in men. Decreased contractility of the detrusor muscle can also make it difficult to effectively empty the bladder, and impossible to fully empty the bladder.

Known causes of urinary retention include bladder issues such as: detrusor sphincter dyssynergia, neurogenic bladder, iatrogenic scarring of the bladder, and other bladder issues Prostate related causes of urinary retention include BPH, prostate cancer, pelvic malignancies, and prostatitis.

Urinary retention is a common pre and post-operative condition that disproportionally impacts older men. Medications are available to aid in voiding but they usually do not result in the voiding of residual bladder urine.

Regardless of any invasive or non invasive surgical procedures, it is common for incomplete bladder emptying to continue with its accompanying urinary urgency and need for double voiding. Hence the invention.

A post-void residual urine of any amount is significant and increases the potential for recurring urinary tract infections stone formation and perhaps most importantly contributes to a lesser quality of life in the day and increased trip to the bathroom at night while trying to sleep. They can also interrupt day time activities.

Most people wake up once or twice during the night. Reasons this might happen include drinking caffeine or alcohol late in the day, a poor sleep environment, a sleep disorder, or another health condition, such as BPH. When a person cannot get back to sleep quickly, that person does not get enough quality sleep to keep refreshed and healthy.

Urinary retention, apart from discomfort and practical quality of life implications, also results in residual urine or urinary stasis, which can lead to an increased risk of urinary tract infection, bladder stones and other consequences such as atrophy of the detrusor muscle, atonic bladder, hypertrophy of the detrusor muscle, diverticula, hydronephrosis (congestion of the kidneys), and others.

BRIEF SUMMARY OF THE INVENTION

The present invention relates, inter alia, to a device to facilitate urination by a male, comprising a vessel having a contact surface area at and adjacent a top edge of the vessel configured to be placed in contact with the penis, the vessel being capable of collecting urine, wherein the contact surface area comprises a thermally conductive material, and wherein the contact surface area has a shape configured to reduce hydrostatic pressure requirements for urination from a standing position as compared with urinating into a toilet from a standing position.

The thermally conductive material may have a thermal conductivity of greater than 20 watts per meter-kelvin.

The contact surface area may be at least 0.5 square inches, preferably at least 1 square inch.

The contact surface area of the vessel may slope inwardly from the top edge of the vessel toward the bottom of the vessel.

When the top edge of the vessel is horizontal, the contact surface area may be at an angle of less than 45° to vertical.

The contact surface area may have an angled, curved or concave shape to increase contact with the penis. The top edge of the vessel may have an hourglass shape comprising two wider portions forming openings separated by a narrower portion.

The contact surface area may comprise at least one material selected from the group consisting of stainless steel, steel, aluminum, tin, copper, nickel, zinc, iron, magnesium and brass.

The vessel may include markings to show volume.

The vessel may comprise an antimicrobial coating on its surfaces.

The contact surface area may comprise a thermally conductive material having a thermal conductivity of at least 20 watts per meter-kelvin. At least some portions other than the contact surface area of the devise may comprise a material having a thermal conductivity less than that of the contact surface area.

The present invention also relates to a method of reducing urinary retention in a male, comprising contacting the penis of the male with a contact surface area of a device and urinating while the male is in a standing position with the penis in contact with the contact surface area, wherein the contact surface area comprises a thermally conductive material and is at an initial temperature at least 14° F. lower than a temperature of the penis.

The device used in the method may be as described above and hereinafter.

The method may further comprise treating the male with a drug therapy selected from the group of alpha blockers, 5α-reductase inhibitors and phosphodiesterase type 5 inhibitors.

The method may further comprise at least one additional urination prior to urinating while the male is in a standing position with the penis in contact with the contact surface area, wherein a void interval between urinations is less than five minutes.

The method may further comprise at least one additional urination prior to urinating while the male is in a standing position with the penis in contact with the contact surface area, wherein a void interval between urinations is less than ten minutes, and the retained urine in the bladder is reduced at least 20% for a given patient population.

DETAILED DESCRIPTION OF THE INVENTION

Figure 1:
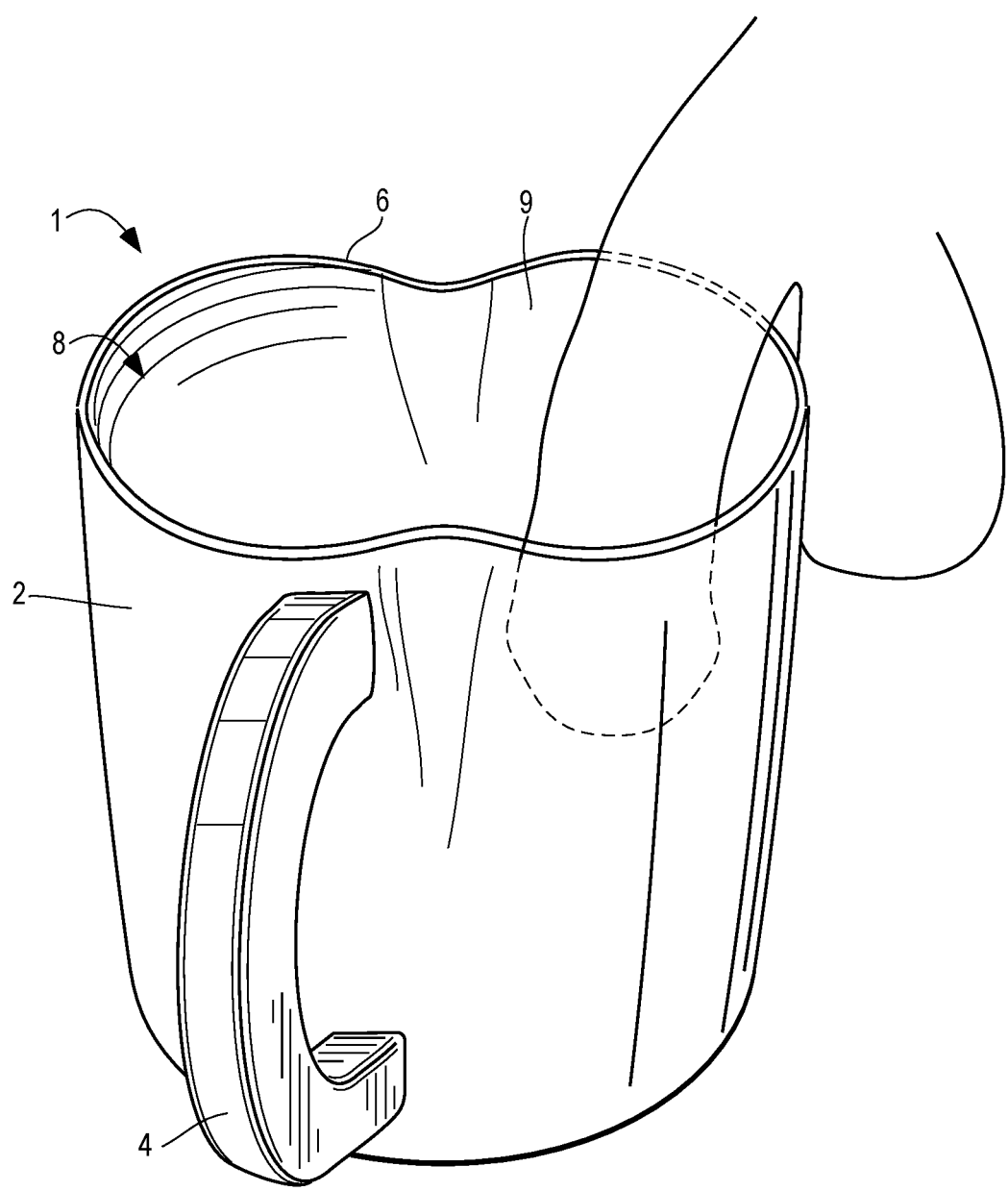
FIG. 1 is a perspective view of an embodiment of the device of the present invention, with penis inserted, using an hourglass (or figure-eight shape) for the vessel for maximal skin exposure.

One embodiment of the invention is a vessel made of a high thermal transfer material, in which is placed the penis of a standing man, preferably with the device touching directly or indirectly the scrotum, transfers heat from the body to the vessel, and assists in passing urine and reducing retention of urine in the bladder. This transfer involves the loss of penile heat (perceived coldness) to the vessel. The device is not intended by itself to be a treatment for BPH but is meant as a key adjunct to medication and surgical type procedures. While the physiological reason for the device assisting in passing urine and reducing retention of urine in the bladder is not completely known, it is postulated that, the device assists in passing urine and reducing retention of urine in the bladder because of thermal conductivity (described hereinafter) and because the hydrostatic pressure of a standing male, whose penis is directed downwards in its natural position, avoids kinks in the urethra when voiding which might otherwise be caused by the growing inelasticity of the male's urethra with aging.

In adults older than 50 years, 30-100 ml or more of residual urine may remain after each voiding because of the decreased contractility of the detrusor muscle or lack of sufficient hydrostatic pressure to expel urine into the toilet bowl. There may be a lack of a stimulus to release the urinary sphincter musculature. In retention, ultrasound of the bladder may show increase in bladder residual urine.

The present invention relates to a non-invasive device that can be used to reduce or eliminate urine retention; we call this device the virtual catheter. The virtual catheter is a vessel used to collect urine, typically from a standing male.

The virtual catheter device, described herein, provides thermal transfer, hydrostatic and unknown neurogenic based stimulus to release the urinary sphincter and initiate urination, and help the user of the virtual catheter to more fully evacuate the bladder of urine.

By placing the penis into the high thermal transfer vessel, made of, e.g., metal such as stainless steel, shaped as to maximize contact with penile skin and, ideally, also directly or indirectly holding the device against the scrotum, preferably while the man is standing, which increases gravitational hydrostatic pressure, it becomes far easier to release the sphincter and void into the vessel and more completely empty the bladder. In terms of temperature, the vessel may be at room temperature let us say 70 degrees F. and the penile and scrotal skin may be at body temperature of approximately 98.6° F. or slightly lower. This effect in the standing position with accompanying increased hydrostatic pressure, causes more complete voiding (though not requiring the pressure required to direct urine to a conventional toilet). The inventors are not aware of this temperature effect ever being used in a method or device for passing urine and/or reducing retention of urine in the bladder. However, an urge to urinate may be experienced by men with BPH when coming inside from a zone of different temperature, such as coming into a warm building from the cold. The neurogenic reason for the temperature effect is not determinable.

Now this non-intrusive device allows for the more complete passage of urine, more complete emptying of the bladder even after a user's double urinary void in the toilet (see testing results discussed below). This is especially useful at night after the double void but is also useful in the daytime after a single void in the toilet and again as can be seen in a test subject. It increases the time interval wherein the urge to void returns. In certain embodiments, in increases the time between voids by many minutes. In addition, it has been found that it can reduce the time interval between the first and second void, (IBD) by use of the vessel described for the second void.

It is a purpose of the virtual catheter device to facilitate urination using thermal conductivity—using a temperature stimulus—on the penis and optionally the scrotum, directly or indirectly, as well as reducing required hydrostatic pressure since the patient is standing and the penis is pointing downward in its usual position therefore avoiding any kinking of the urethra in the older individual with less tissue elasticity There is a need for a non-invasive treatment to reduce urinary retention.

It is an object of certain embodiments of the present invention to assist a patient in more consistently evacuating the bladder, i.e., substantially reducing or eliminating retained urine in the bladder. Retained urine volume may be, for a given urination protocol, may be reduced at least 10%, preferably at least 20%, more preferably at least 30%, most preferably at least 40% for a given patient population.

It is an object of certain embodiments of the present invention to extend or prolong sleeping intervals for patients that are otherwise awoken by urinary urgency, including inter alia users who suffer with BPH. With consistent use, average sleep times may be increased by fifteen minutes or more, preferably thirty minutes or more, most preferably forty-five minutes or more.

Shortening double or triple void times can make it easier for patients to fall back asleep by reducing the period of time between voids during which time a patient may become distracted, become fully awake, and have a harder time falling back asleep. This reduces their total sleep time. Such periods of being awake may also reduce the activity of antidiuretic hormone (ADH).

Normally, the amount of ADH in the body is higher during the night. This helps prevent urination while you are sleeping. But if the levels of ADH remain low during the night, the body will produce large amounts of urine, so urination during the night is more likely. Hence the importance of the reduced DVI so as to not reduce ADH formation.

It is an object of certain embodiments of the present invention to prolong intervals between urination sessions during daytime hours for users of the virtual catheter. With consistent use, average urinary intervals may be increased by fifteen minutes or more, preferably thirty minutes or more, most preferably forty-five minutes or more.

It is an object of certain embodiments of the present invention to reduce the risk (and frequency) of urinary tract infections (UTI). It is an object of embodiments of the present invention to reduce the prevalence of UTI in adult males (including adult males with BPH) by at least 15%, preferably by at least 20%, most preferably by at least 25%, as compared with a similarly aged, healthy control group.

It is an object of certain embodiments of the present invention to reduce urinary tract infections.

It is an object of certain embodiments of the present invention to reduce or eliminate the formation of bladder stones, through a modality of reducing or eliminating retained urine. It is an object of certain embodiments of the present invention to reduce the incidence of bladder calculi in men with BPH by at least 2.5%, preferably by at least 10%, most preferably by at least 20%, as compared with a similarly aged, control group not using the virtual catheter.

It is an object of certain embodiments of the present invention to reduce or eliminate the need for conventional catheter placement after certain urological procedures, increasing patient comfort, decreasing the need for follow on medical care, and reducing the risk of scarring and other tissue damage for urethral catheter insertion.

It is an object of certain embodiments of the present invention to employ the virtual catheter as a diagnostic device to ascertain retained urine after conventional urination (potentially replacing the need for ultrasound or other imaging to determine retained urine after the patient pees).

It is an object of certain embodiments of the present invention to allow a user of the virtual catheter to track urine collection over time.

It is an object of the invention to reduce the time interval between double voiding, the double voiding interval (DVI). Double voiding is almost universally recommended in all patients with BPH.

In certain embodiments, the virtual catheter is prescribed for a patient in conjunction with a pharmaceutical agent, including without limitation, one or more of: alpha blockers such as tamsulosin, 5α-reductase inhibitors such as finasteride, and phosphodiesterase type 5 inhibitors, such as tadalafil. In certain embodiments, the virtual catheter is prescribed together with one or more of the above-reference drugs, optionally as a drug-device combination.

Embodiments of the present invention promote more complete urinary flow and prevent dribbling.

Embodiments of the present invention comprise a non-invasive device that is placed in contact with the penis prior to, and during, urination.

Typically, the user's urine is collected in the device, and then emptied by the user.

Typically, the device is used by a standing user, but it is possible to use the device in a non-standing position. The ability to stand using the virtual catheter is a significant advantage; many older males find it uncomfortable to repeatedly sit and stand from the toilet, particularly in view of their frequent urination patterns.

Embodiments of the present invention comprise a cup or vessel. Optionally, the outer margin is ergonomically designed to increase surface area contact between the upper edge of the cup shaped device and the penis. Optionally, the upper, inner portion is ergonomically designed to increase surface area contact between the upper, inner portion of the cup shaped device and the penis.

Two mechanisms are employed, which are both novel to the literature and medical practice.

The first mechanism is the use of a temperature differential as a stimulus. The second mechanism is in the reduction of required hydrostatic pressure. The combination of these two mechanisms provides improved results.

In embodiments of the present invention, the penis is placed against a material that is lower in temperature surface body temperature (here, temperature of the penis). This temperature differential is preferably at least 15° F., preferably at least 20° F., more preferably at least 25° F., and most preferably at least 35° F.

Normal temperature of a flaccid penis is 91.7° F. to 92.8° F., as reported in the literature. Thus, a cup shaped device at ambient temperature of 75° F. will have a temperature differential with the penis of approximately 17° F. Now, according to Vivint.com, the average ambient temperature of a home is 68 to 76 degrees (https://www.vivint.com/resources/article/best-home-room-temperature—link retrieved on Jun. 7, 2021). The result is that ambient temperature in a home will tend to generate a significant temperature differential.

Preferably, the temperature differential is 15-40° F., preferably 25-35° F.

Rarely, it may be advantageous to chill the virtual catheter to temperatures below ambient temperatures. In such cases where the virtual catheter is chilled, a larger temperature differential will be achieved, i.e., a temperature differential of greater than 40° F.

In certain embodiments, some are all of the material comprising the contact surface with the penis, are selected for thermal conductive properties. Generally, the higher the thermal conductive properties, the greater the effect of the temperature differential on promoting urinary flow.

Preferably, the contact surface area is comprised in part, substantially or entirely, of a material with a high thermal conductivity, measured in watts per meter-kelvin, of greater than 20, preferably greater than 100, more preferably greater than 200, and most preferably greater than 300 watts per meter-kelvin.

A preferred thermal conductivity range for the contact surface area is 20 to 500 watts per meter-kelvin.

Generally, the contact surface area must be adequate to provide a sufficient temperature-based stimulus.

In certain embodiments, the contact surface area between the vessel and the penis is at least 0.5 inch$^2$, preferably at least 0.75 inch$^2$, more preferable at least 1 inch$^2$, and most preferably at least 1.25 inch$^2$, measured as an average for a typical group of users.

In other embodiments, the internal wall of the virtual catheter will be sloped inwards to accommodate contact area between member and receptable wall, i.e. the penis is supported on the inward-sloping surface. Preferably, substantially all or all of the contact surface area is a high thermally conductive material.

In other embodiments, the virtual catheter will comprise a short ramp portion, akin to a ski jump, to accommodate the member and provide additional contact surface area. The ski jump is angled downwards from the plane of the top of the virtual catheter, in most embodiments. Generally, it is desirable that the "ski jump" be short enough for the tip of the penis to extend past it. The "ski jump" may be concave in shape to facilitate additional contact surface between penis and the "ski jump".

Concave, curved, or angled shapes to promote contact surface area may be employed in various designs. The vessel may use a tighter curve to increase contact surface area; a figure eight shape may be useful to have two ends with a tighter curve than would be the case for a comparably sized cylindrical design. and the handle convenient for a right or left handed person.

The geometry of the virtual catheter is important. As a receptable, the virtual catheter has a receptable function and typically will take the general form of a cup. It is not necessary for the virtual catheter to take the form of a cup, as the essential functionality is delineated above as a function of temperature stimulation and reducing hydrostatic pressure requirements.

The virtual catheter may channel urine into a toilet or other proper sewer, e.g., by means of a tube extending from the bottom of the vessel; it may use a separate disposable collection depot like a conventional catheter bag, provided that the virtual catheter has the ability to provide temperature stimulation to the penis and reduce hydrostatic pressure requirements. It is conceivable that the device and method of the invention can use a tube having thermal conductive properties configured to be placed around the shaft of the penis during urination. Nonetheless, a cup like shape is the preferred embodiment.

In preferred embodiments, the weight of the virtual catheter should be comfortable to hold. Typically, the virtual catheter will have at least one external handle. The virtual catheter may have more than one external handle, for example and without limitation, two handles.

The virtual catheter is intended for use when the patient is standing.

Stainless steel, steel, aluminum, tin, copper, nickel, tin, zinc, iron, magnesium, and brass are non-limitative examples of materials that may be employed for the contact surface area.

In certain embodiments, the vessel may be comprised of different materials or difference surfaces. As a non-limitative, example, the vessel may have a contact surface area made from stainless steel and the rest of the vessel may be made from a plastic.

The interior of the cup device may be scored or otherwise marked to show volume of collected urine. The exterior of the cup may be scored or otherwise marked or designed to show volume of collected urine, particularly where the cup has a transparency to see the internal amount.

In certain embodiments, the device has a white interior in whole or in part (e.g., on the bottom) to facilitate colorometric analysis of the urine.

In certain embodiments, the device may be clear or transparent in whole or in part (e.g., on the bottom) to facilitate colorometric analysis of the urine. The device may comprise a light source to facilitate colorometric analysis.

In certain embodiments, the vessel is treated in whole, in part, or substantially with an antimicrobial coating, it being noted that it is important not to adversely affect the thermal conductive properties of the contact area in preferred embodiments.

As an alternative to coatings, materials may be employed which themselves have antimicrobial activity, e.g., copper.

In certain embodiments, the virtual catheter device may comprise a sensor to measure urine collected. The device may comprise a clock or timer to record the time of urine collections. The device may comprise a dissolved solids meter. The device may comprise a thermistor or temperature sensor. The device may contain optical sensors, or other sensors to determine the value of an analyte. The device may contain a camera. The cup device may have wife, Bluetooth, cellular, or other connectivity. The device may be capable of using connectivity to convey the time, amount, temperature, dissolved solids, analyte levels, analyte measurements or other collected information to a database. Such a database may be in the cloud, on a computer, a phone or app. The database may be accessible by a patient, caregiver, physician, or other medical professional, and may be subject to pre-set alerts. Particularly as it relates to alerts, the contents of the present applicant's U.S. Pat. No. 7,824,612 are hereby incorporated by reference herein as if fully set forth herein.

In certain embodiments, the device may receive reagent sticks or strips for diagnostic purposes.

In certain embodiments, the device may have a high thermal conductivity neck with an accordion like bottom so that it is more portable for travel.

In certain embodiments, the device has a vibratory feature for additional stimulus. The vibratory feature may be turned on using a button, or automatically be triggered by a light sensor, motion sensor, liquid sensor, or other sensor. Optionally, the device comprises a power source.

The virtual catheter may be supplied as part of a kit with specific cleaning materials and procedures. The virtual catheter may alternatively be supplied with a cleansing device that is capable of adequately cleaning and/or sterilizing the device. Cleansing methods may include the use of temperature, cleaning agents, and ultraviolet or other light wavelengths.

It is advantageous that the urinary virtual catheter be readily identifiable for its intended use, and not readily confusable with other items. Markings, indicia, and colors may be used for this purpose.

It is important to note that urine is normally free of bacterial contamination. In certain instances, in emergency situations, it has been recommended to clean a wound with one's own urine.

In certain embodiments, the virtual catheter is a disposable, single use device. Typically, the single use version will have a metal rim, with a paper or plastic lower collection portion.

Optionally, the single use device folds like an accordion, or otherwise can be folded or compacted for ease of portability before use.

FIG. 1 is a perspective view of one embodiment of the device of the present invention, with penis inserted, using a figure-eight shape for the vessel. The device 1 of this embodiment includes a vessel 2 having a handle 4. An upper lip or edge 6 of the vessel 2 forms an opening 8. The upper lip or edge 6 of the vessel 2 forming the opening 8 (and cross-sectional shapes of the vessel 2 for at least a portion of the vessel adjacent the top edge 6, in planes substantially parallel to an upper lip/opening 6) may have, as shown in FIG. 1, an hourglass (or figure eight-like shape), i.e., two wider portions separated by a narrower portion. It is preferable but not required for the device 1 to include a handle 4. This shape allows for holding and use of the device by a right or left handed person.

The hourglass (or figure eight-like shape), or other concave, curved, or angled shapes promote greater contact surface area with the penis. The vessel 2 or at least the portion extending downward from the upper lip or edge 6 may use a tighter curve than that shown in FIG. 1 to increase contact surface area; a figure eight shape may be useful to have two ends with a tighter curve than would be the case for a comparably sized cylindrical design.

The internal wall 9 of the virtual catheter may be sloped inwardly from a top edge of the vessel to accommodate contact area between the penis and the receptable wall, i.e., it is configured for the penis to be supported on the inward-sloping surface. Preferably, substantially all or all of the contact surface area (area configured to be in contact with the penis and optionally the scrotum) or optionally all of the device 1 is made of or coated with a high thermally conductive material. Metals such as stainless steel, steel, aluminum, tin, copper, nickel, tin, zinc, iron, magnesium (or its alloys or compounds), and brass are non-limitative examples of materials that may be employed for at least the contact surface area.

Figure 2A:
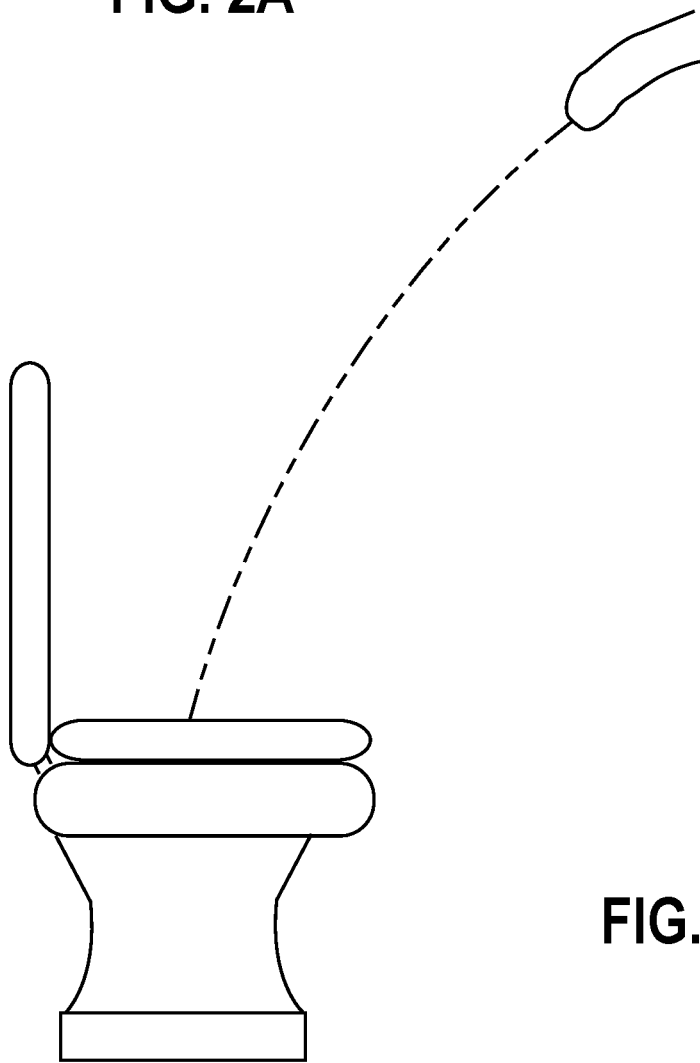
FIGS. 2A and 2B contrast the urine stream pressure required to reach a toilet from standing position (FIG. 2A) and the pressure required to urinate in the device of the present invention (FIG. 2B).
Figure 2B:
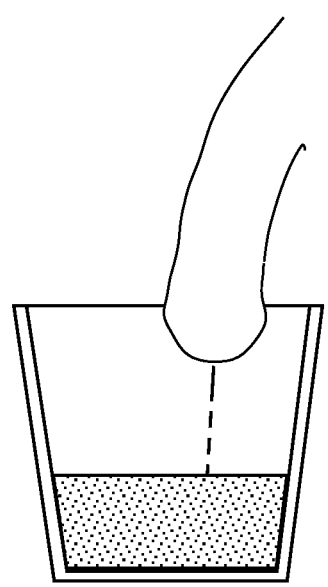

FIGS. 2A and 2B contrast the urine stream pressure illustrated with broken lines (and angle of the penis with respect to the vertical) required to reach a toilet from standing position (FIG. 2A) and the urine stream pressure illustrated with broken lines (and angle of the penis with respect to the vertical) required to urinate in the device of the present invention (FIG. 2B). As can be seen, the device can reduce the hydrostatic pressure necessary to expel urine as compared to reaching a toilet from standing position.

Figure 3:
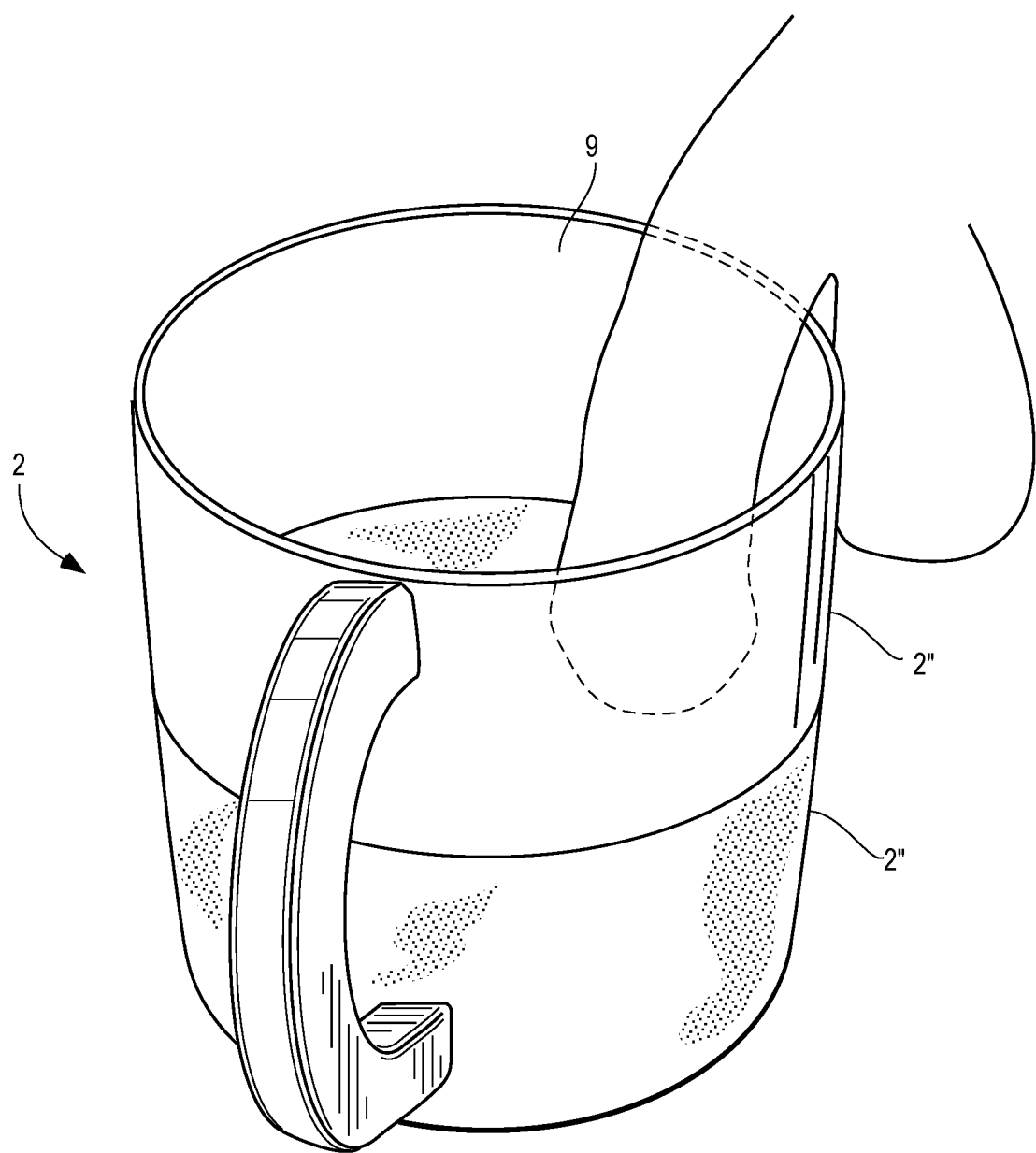
FIG. 3 is a device that is made from two distinct materials.

In certain embodiments, the vessel 2 may be comprised of different materials or different surfaces. As a non-limitative example, as shown in FIG. 3, the vessel 2 may have a contact surface area 2 inches sq made from a material with high thermal conductivity such as stainless steel and the non-contact portions 2" of the vessel may be made from less thermally conductive material such as plastic. Preferably, the contact surface area 2' has a high thermal conductivity, measured in watts per meter-kelvin, of greater than 20, preferably greater than 100, more preferably greater than 200, and most preferably greater than 300 watts per meter-kelvin.

The non-contact portion 2" of the vessel has a low thermal conductivity, measured in watts per meter-kelvin, of less than 20, preferably less than 10, more preferably less than 2, and most preferably less than 1 watt per meter-kelvin. Many plastics have a thermo-conductivity of less than 1 watt per meter-kelvin.

Figure 4:
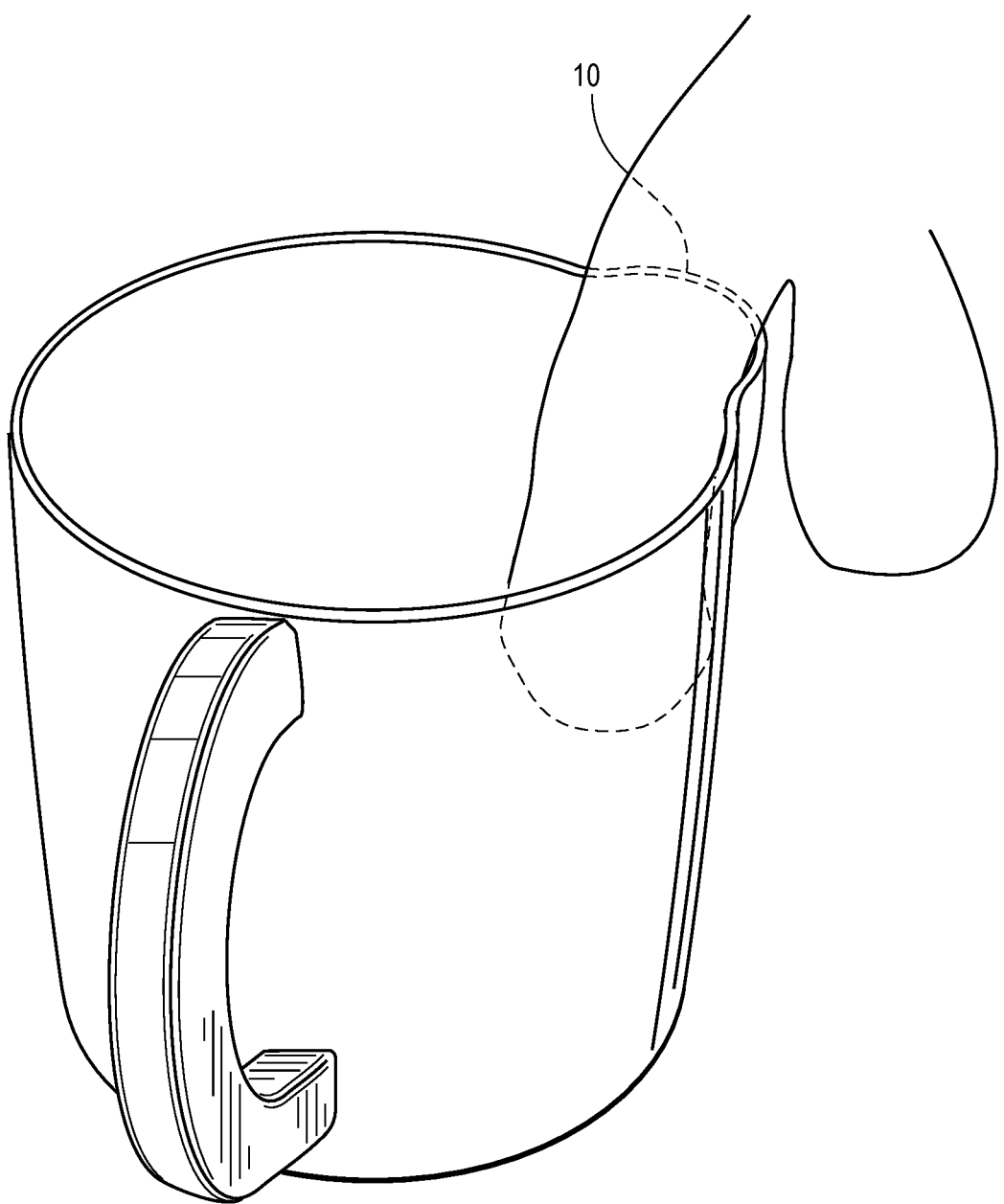
FIG. 4 is a device with a curved area to increase surface contact with the penis.

FIG. 4 shows a device with a curved area 10 having a radius of curvature similar to a radius of curvature of a flaccid penis configured to increase surface contact with the penis.

Figure 5:
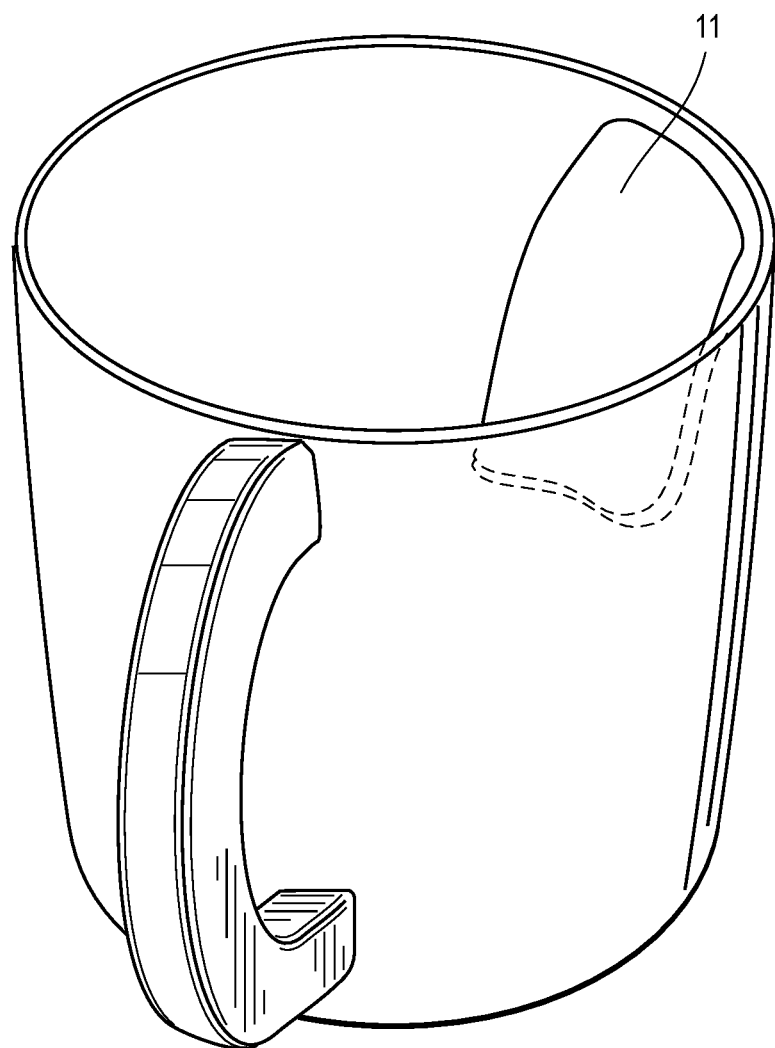
FIG. 5 has a "ski slope" feature to increase surface contact area with the penis.

FIG. 5 shows an embodiment having a sloped portion 11 or "ski slope" feature configured to increase surface contact area with the penis.

In certain embodiments, the internal wall 9 of the vessel 2 (or the curved area 10 or sloped portion 11) on which the penis rests is sloped inwardly from a top edge of the vessel 2 toward the bottom such that, when the upper edge 6 and bottom surface of the vessel 2 is horizontal, the internal wall 9 of the vessel 2 (or the curved area 10 or sloped portion 11) is not vertical but is at a downward angle of less than 45°, more preferably less than 35°, even more preferably less that 30° to vertical. By inward angle slope, we mean the slope measured from the top of the vertical axis at the side of the vessel, inwards. The embodiment of FIG. 2B has a very modest inward slope, substantially less than 30 degrees.

As noted infra, an inward slope may be a straight angle, but it may also be a generally sloped surface that is curved or otherwise angled or not shaped as a pure slope (see, e.g., FIG. 4).

In certain embodiments, the vessel can have an opening or openable drain near or in a bottom surface of the vessel to drain the urine from the vessel. The drain may further connect to a tube, or a secondary collection chamber, or other suitable receiving area for the urine.

It is contemplated that embodiments of the present invention may be used with various double and triple void techniques.

A non-limitative series of triple urinary iterations are contemplated including inter alia: (i) toilet, toilet, vessel; (ii) toilet, vessel, vessel; (iii) vessel, vessel, vessel. A non-preferred sequence is (iv) vessel, vessel, toilet, or (v) vessel, toilet, toilet. These triple urinary sequences are preferably completed within a total of fifteen minutes, preferably within ten minutes, more preferably within seven minutes.

A non-limitative series of double urinary iterations are contemplated including inter alia: (i) toilet, vessel; and (ii) vessel, vessel. A non-preferred sequence is vessel, toilet. These double urinary sequences are preferable completed within a total of twelve minutes, preferably within ten minutes, more preferably within five minutes, and most preferably within three minutes.

The void interval is the time between voids. Preferably, the void interval is less than ten minutes, preferably less than five minutes, and most preferably less than three minutes. The use of the vessel of the current invention allows for such brief effective void intervals, with substantial urine expulsion and minimizing retained urine.

The short duration of the complete sequences is particularly desirable to facilitate sleep, or to permit uninterrupted time during the day.

Embodiments of the present invention may be adapted for use by females.

Example A

This experiment will have 3 cups: one plastic (low thermal conductivity); one stainless steel (moderate thermal conductivity); and one copper (high thermal conductivity).

A ETEKCITY model 774 infrared thermometer was used in this experiment.

The cups were stored at room temperature ambient conditions and a temperature reading of each cup was taken with the following results: Plastic-72 F; Stainless Steel-72 F; and Copper-72 F Next, a finger of an adult male was measured (as proxy for the penis) and showed a temperature of 92 F Then, the finger was placed in the inside of each cup, and the adult male's temperature impression was recorded: (i) finger placed on inside of Plastic Cup . . . no distinct temperature feeling; (ii) finger placed on inside of Stainless Steel Cup distinct feeling of coolness; (3) finger placed on inside of Copper Cup . . . distinct and heightened feeling of cool/cold.

The conclusion of this experiment is that thermal conductivity is related to temperature perception/nervous system response.

Example B

In this example, an approximately 80-year old male, with BPH, volunteered to use a stainless steel vessel and a copper vessel supplied to him, and record his results. By "use" the volunteer was instructed to urinate into the vessel while his penis was touching the inner lid.

As shown below, he typically voided his bladder as per his personal routine in the toilet, and then afterwards used the provided vessel. He reported his results as follow, with SS denoting stainless steel, and cu denoting copper. All voids were made standing. After urination in the vessel, the volunteer emptied the vessel into a scored beaker to measure the volume of evacuated urine. The volume figure is the urine collected in the vessel.

First Session, Example B

| 1st go ---- toilet | 11:30 p.m. | |
|---|---|---|
| 2nd go --- SS Cup | 11:40 p.m. | 70 ml |
| 1st go ---- toilet | 1:50 a.m | |
| 2nd go --- SS Cup | 2:01 a.m. | 85 ml. |
| 3rd go ---- SS Cup | 2:07 a.m. | 50 ml |
| 1st go ---- toilet | 5:03 a.m. | |
| 2nd go --- SS Cup | 5:13 a.m. | 125 ml |
| 1st go ---- toilet | 7:06 a.m. | |
| 2nd go --- SS Cup | 7:18 a.m. | 85 ml |
| Day | | |
| 1st go ---- toilet | 2:45 p.m. | |
| 2nd go --- SS Cup | 2:53 p.m. | 50 ml |

Second Session, Example B

| 1st go | 12:25 | toilet | |
|---|---|---|---|
| 2nd go | 12:34 | SS Cup | 80 ml |
| 3rd go | 12:42 | SS Cup | 50 ml |
| 1st go | 2:20 | toilet | |
| 2nd go | 2:30 | SS Cup | 115 ml |
| 3rd go | 2:44 | SS Cup | 40 ml |
| 1st go | 4:25 | toilet | |
| 2nd go | 4:36 | SS Cup | 80 ml |
| 3rd go | 4:47 | SS Cup | 40 ml |
| 1st go | 7:24 | toilet | |
| 2nd go | 7:34 | SS Cup | 80 ml |
| 3rd go | 7:45 | SS Cup | 35 ml |
| DAY | | | |
| 1st go | 1:00 p.m. | toilet | |
| 2nd go | 1:10 p.m. | SS Cup | 50 ml |
| 3rd go | 1:21 p.m. | SS Cup | 50 ml |

Third Session, Example B

| 1st go ---- toilet | 11:30 p.m. | |
|---|---|---|
| 2nd go --- toilet | 11:35 p.m. | |
| 3rd go ---- SS Cup | 11:41 p.m. | 50 ml |
| 1st go ---- toilet | 1:35 a.m. | |
| 2nd go --- toilet | 1:47 a.m. | |
| 3rd go ---- SS Cup | 1:55 a.m. | 40 ml |
| 1st go ---- toilet | 3:28 a.m. | |
| 2nd go --- toilet | 3:35 a.m. | |
| 3rd go ---- SS Cup | 3:45 a.m. | 50 ml |
| 1st go ---- toilet | 5:40 a.m. | |
| 2nd go --- toilet | 5:47 a.m. | |
| 3rd go ---- SS Cup | 5:55 a.m. | 60 ml |
| Day | | |
| 1st go ---- toilet | 2:30 p.m. | |
| 2nd go --- toilet | 2:40 p.m. | |
| 3rd go ---- SS Cup | 2:47 p.m. | 80 ml |

Fourth Session, Example B

| 1st go | 11:40 p.m. | toilet | |
|---|---|---|---|
| 2nd go | 11:50 p.m. | toilet | |
| 3rd go | 12:05 a.m. | SS Cup | 30 ml |
| 1st go | 2:15 a.m. | toilet | |
| 2nd go | 2:22 a.m. | toilet | |
| 3rd go | 2:30 a.m. | SS Cup | 40 ml |
| 1st go | 4:30 a.m. | toilet | |
| 2nd go | 4:37 a.m. | toilet | |
| 3rd go | 4:44 a.m. | SS Cup | 60 ml |
| 1st go | 6:20 a.m. | toilet | |
| 2nd go | 6:25 a.m. | toilet | |
| 3rd go | 6:30 a.m. | SS Cup | 40 ml |
| Day | | | |
| 1st go | 2:10 p.m. | toilet | |
| 2nd go | 2:15 pm | SS Cup | 110 ml |

Fifth Session, Example B

| 1st go | 12:37 a.m. | toilet | |
|---|---|---|---|
| 2nd go | 12:44 a.m. | toilet | |
| 3rd go | 12:54 a.m. | SS Cup | 50 ml |
| 1st go | 3:40 a.m. | toilet | |
| 2nd go | 3:47 a.m. | toilet | |
| 3rd go | 3:55 a.m. | SS Cup | 60 ml |
| 1st go | 6:15 a.m. | toilet | |
| 2nd go | 6:22 a.m. | toilet | |
| 3rd go | 6:33 a.m. | SS Cup | 40 ml |
| Day | | | |
| 1st go | 2:30 p.m. | toilet | |
| 2nd go | 2:37 p.m. | SS Cup | 75 ml |

Sixth Session, Example B

| 1st go | 12:15 a.m. | toilet | |
|---|---|---|---|
| 2nd go | 12:25 a.m. | toilet | |
| 3rd go | 12:34 a.m. | SS Cup | 60 ml |
| 1st go | 2:55 a.m. | toilet | |
| 2nd go | 3:05 a.m. | toilet | |
| 3rd go | 3:14 a.m. | SS Cup | 50 ml |
| 1st go | 5:25 a.m. | toilet | |
| 2nd go | 5:34 a.m. | toilet | |
| 3rd go | 5:42 a.m. | SS Cup | 40 ml |
| Day | | | |
| 1st go | 3:05 p.m. | toilet | |
| 2nd go | 3:16 p.m. | SS Cup | 60 ml |

Seventh Session, Example B

| 1st go | 12:10 a.m. | toilet | |
|---|---|---|---|
| 2nd go | 12:19 a.m. | toilet | |
| 3rd go | 12:28 a.m. | SS cup | 50 ml |
| 1st go | 3:58 a.m. | toilet | |
| 2nd go | 4:10 a.m. | toilet | |
| 3rd go | 4:18 a.m. | SS Cup | 55 ml |
| 1st go | 6:20 a.m. | toilet | |
| 2nd go | 6:26 a.m. | toilet | |
| 3rd go | 6:36 a.m. | SS Cup | 50 ml |
| Day | | | |
| 1st go | 3:10 p.m. | toilet | |
| 2nd go | 3:20 p.m. | SS Cup | 110 ml |

Eighth Session, Example B

| 1st go | 12:38 a.m. | toilet | |
|---|---|---|---|
| 2nd go | 12:45 a.m. | toilet | |
| 3rd go | 12:54 a.m. | Cu Cup | 35 ml |
| 1st go | 2:35 a.m. | toilet | |
| 2nd go | 2:45 a.m. | toilet | |
| 3rd go | 2:54 a.m. | Cu Cup | 50 ml |

-continued

| | | | |
|---|---|---|---|
| 1st go | 5:32 a.m. | toilet | |
| 2nd go | 5:42 a.m. | toilet | |
| 3rd go | 5:50 a.m. | Cu Cup | 45 ml |
| Day | | | |
| 1st go | 2:25 p.m. | toilet | |
| 2nd go | 2:30 p.m. | Cu Cup | 60 ml |

Ninth Session, Example B

| | | | |
|---|---|---|---|
| 1st go | 12:10 a.m. | toilet | |
| 2nd go | 12:20 a.m. | toilet | |
| 3rd go | 12:35 a.m. | Cu Cup | 40 ml |
| 1st go | 3:25 a.m. | toilet | |
| 2nd go | 3:30 a.m. | toilet | |
| 3rd go | 3:37 a.m. | Cu Cup | 55 ml |
| 1st go | 5:55 a.m. | toilet | |
| 2nd go | 6:07 a.m. | toilet | |
| 3rd go | 6:14 a.m. | Cu Cup | 35ml |
| Day | | | |
| 1st go | 3:50 p.m. | toilet | |
| 2nd go | 4:05 p.m. | Cu cup | 50 ml |

Tenth Session, Example B

| | | | |
|---|---|---|---|
| 1st go | 11:30 p.m. | toilet | |
| 2nd go | 12:10 a.m. | toilet | |
| 3rd go | 12:20 a.m. | Cu Cup | 40 ml |
| 1st go | 3:15 a.m. | toilet | |
| 2nd go | 3:22 a.m. | toilet | |
| 3rd go | 3:29 a.m. | Cu Cup | 40 ml |
| 1st go | 5:10 a.m. | toilet | |
| 2nd go | 5:19 a.m. | toilet | |
| 3rd go | 5:30 a.m. | Cu Cup | 50 ml |
| Day | | | |
| 1st go | 4:00 p.m. | toilet | |
| 2nd go | 4:10 p.m. | Cu cup | 60 ml |

Eleventh Session, Example B

| | | | |
|---|---|---|---|
| 1st go | toilet | 1:25 a.m. | |
| 2nd go | toilet | 1:32 a.m. | |
| 3rd go | Cu Cup | 1:45 a.m. | 75 ml |
| 1st go | toilet | 6:15 a.m. | |
| 2nd go | toilet | 6:28 a.m. | |
| 3rd go | Cu Cup | 6:44 a.m. | 60 ml |
| Day | | | |
| 1st go | toilet | 4:04 p.m. | |
| 2nd go | Cu cup | 4:12 p.m. | 60 ml |

Some observations are in order concerning the results of Example B. First, the test volunteer reported reduced fluid intake at the time of the switch from the stainless steel vessel to the copper vessel. Accordingly, this experiment was not taken to have bearing on the efficacy of these two materials.

The fact that the test subject was able to reliably expel a substantial amount of urine routinely, even after two conventional voidings in a short period point to retained urine after normal voiding. This retain urine was substantially eliminated through use of the virtual catheter, when we compare the volume of that void to the retain urine volumes described in the literature.

The test subject reported longer intervals between urination while using the virtual catheter, and longer sleep intervals: " . . . good uninterrupted sleep."

Example C

In this example, an approximately 80-year old male, with BPH, volunteered to use a copper vessel supplied to him, and record his results. By "use" the volunteer was instructed to urinate into the vessel while his penis was touching the inner lid.

As shown below, he typically voided his bladder one time routine in the toilet, and then promptly afterwards used the provided vessel (within three minutes). Both voids were made standing. After urination in the vessel, the volunteer emptied the vessel into a scored beaker to measure the volume of evacuated urine. Reports are reported below. The volume figure is the urine collected in the vessel.

| | | | |
|---|---|---|---|
| 1. toilet | 10:05 | | |
| 2. Cup | 10:06:30 | 65 ml | 1½ minute interval |
| 1. toilet | 1:10 a.m. | | |
| 2. cup | 1:12 a.m. | 70 ml | 2 minute interval |
| 1. toilet | 3:45 a.m. | | |
| 2. cup | 3:48 a.m. | 40 ml | 2½ minute interval |
| 1. toilet | 6:30 a.m. | | |
| 2. cup | 6:32 a.m. | 60 ml | 2 minute interval |
| 1. toilet | 10:05 p.m. | | |
| 2. Cup | 10:06 p.m. | 65 ml | 1½ minute interval |
| 1. toilet | 1:10 a.m. | | |
| 2. cup | 1:12 a.m. | 70 ml | 2 minute interval |
| 1. toilet | 3:45 a.m. | | |
| 2. cup | 3:48 a.m. | 40 ml | 2½ minute interval |
| 1. toilet | 6:30 a.m. | | |
| 2. cup | 6:32 a.m. | 60 ml | 2 minute interval |

The user from these tests reported that the device allowed him to shorten his typical interval between successful double voids (DBI). By successful, we mean a void resulting in a substantial amount of urine, i.e. more than 30 ml. When urinating in a toilet, the user reported that additional time was often required for a successful second or double void.

Example D

In this example, an approximately 80-year old male, with BPH, volunteered to use a copper vessel supplied to him, and record his results. By "use" the volunteer was instructed to urinate into the vessel while his penis was touching the inner lid.

As shown below, he typically voided his bladder one time routine in the toilet (T), and then promptly afterwards used the provided copper vessel (Cu) (within three minutes) a first time, and then a second time within an additional three minutes. All voids were made standing. After urination in the vessel, the volunteer emptied the vessel into a scored beaker to measure the volume of evacuated urine. Reports are reported below. The volume figure is the urine collected in the vessel for each urination.

| | | | |
|---|---|---|---|
| 11:25 pm | T | | |
| 11:27 pm | Cu | 110 ml | 3 minutes |
| 11:30 pm | Cu | 30 ml | 2 minutes |
| 3:15 am | T | | |
| 3:18 am | Cu | 70 ml | 3 minutes |
| 3:21 am | Cu | 30 ml | 3 minutes |
| 5:50 am | T | | |
| 5:34 am | Cu | 30 ml | 2 minutes |
| 5:37 am | Cu | 20 ml | 3 minutes |

The test subject noted with great pleasure that he was able to get nearly four hours of sleep (over three and a half hours) between the last evening void and his first void during the night/early morning. The most important issue here is the reduced MT or 'double voiding interval'. Normally this individual would wait 10 or more minutes between the double void. Sleep studies show the longer sleep is interrupted the more difficult it is to again fall asleep. This advantage was stated by the test subject.

What is claimed is:

1. A device to facilitate urination by a male, comprising a vessel having a contact surface area at and adjacent a top edge of the vessel configured to be placed in contact with the penis, the vessel being capable of collecting urine, wherein the contact surface area comprises a thermally conductive material having a thermal conductivity of at least 20 watts per meter-kelvin, and wherein, when the top edge of the vessel is horizontal, the contact surface area of the vessel slopes inwardly starting from the top edge of the vessel toward the bottom of the vessel to reduce urine stream pressure requirements.

2. The device according to claim 1, wherein the contact surface area is at least 0.5 square inches.

3. The device according to claim 1, wherein the contact surface area is at least 1 square inch.

4. The device according to claim 1, wherein, when the top edge of the vessel is horizontal, the contact surface area is at an angle of less than 45° to vertical.

5. The device according to claim 1, wherein the top edge of the vessel has an hourglass shape comprising two wider portions forming openings separated by a narrower portion.

6. The device according to claim 1, wherein the contact surface area comprises at least one material selected from the group consisting of stainless steel, steel, aluminum, tin, copper, nickel, zinc, iron, magnesium and brass.

7. The device according to claim 1, wherein the vessel includes markings to show volume.

8. The device according to claim 1, wherein the vessel comprises an antimicrobial coating on its surfaces.

9. The device according to claim 1, wherein at least some portions other than the contact surface area comprises a material having a thermal conductivity less than that of the contact surface area.

10. A method of reducing post-void residual urine in a male with BPH, comprising contacting the penis of the male with BPH with a contact surface area of a device and urinating while the male is in a standing position with the penis in contact with the contact surface area, wherein the contact surface area comprises a thermally conductive material having a thermal conductivity of at least 20 watts per meter-kelvin and is at an initial temperature at least 14° F. lower than a temperature of the penis, the contact surface area and initial temperature being capable of producing sufficient thermal transfer to release the urinary sphincter and initiate urination.

11. The method according to claim 10, wherein the device comprises a vessel having the contact surface area at and adjacent a top edge of the vessel, the vessel being capable of collecting urine.

12. The method according to claim 11, wherein the contact surface area is at least 0.5 square inches.

13. The method according to claim 11, wherein the contact surface area is at least 1 square inch.

14. The method according to claim 11, wherein the contact surface area of the vessel slopes inwardly from the top edge of the vessel toward the bottom of the vessel.

15. The method according to claim 14, wherein, when the top edge of the vessel is horizontal, the contact surface area is at an angle of less than 40° to vertical.

16. The method according to claim 11, wherein the contact surface area has an angled, curved or concave shape to increase contact with the penis.

17. The method according to claim 11, wherein the top edge of the vessel has an hourglass shape comprising two wider portions forming openings separated by a narrower portion.

18. The method according to claim 11, wherein the contact surface area comprises at least one material selected from the group consisting of stainless steel, steel, aluminum, tin, copper, nickel, zinc, iron, magnesium and brass.

19. The method according to claim 10, wherein the vessel includes markings to show volume.

20. The method according to claim 10, wherein the vessel comprises an antimicrobial coating on its surfaces.

21. The method according to claim 10, wherein at least some portions other than the contact surface area comprises a material having a thermal conductivity less than that of the contact surface area.

22. The method according to claim 10, further comprising treating the male with a drug therapy selected from the group of alpha blockers, 5α-reductase inhibitors and phosphodiesterase type 5 inhibitors.

23. The method of claim 10, further comprising at least one additional urination prior to urinating while the male is in a standing position with the penis in contact with the contact surface area, wherein a void interval between urinations is less than five minutes.

24. The method of claim 10, further comprising at least one additional urination prior to urinating with the penis in contact with the contact surface area, wherein a void interval between urinations is less than ten minutes, and the retained urine in the bladder is reduced at least 20% for a given patient population.

* * * * *